United States Patent [19]

Wentland et al.

[11] 4,439,436

[45] Mar. 27, 1984

[54] 1,3-DIOXOLO(4,5-G)QUINOLINE COMPOUNDS

[75] Inventors: Mark P. Wentland, North Greenbush; Denis M. Bailey, East Greenbush, both of N.Y.

[73] Assignee: Sterling Drug Inc., New York, N.Y.

[21] Appl. No.: 405,263

[22] Filed: Aug. 4, 1982

[51] Int. Cl.$^3$ .................. C07D 491/04; A61K 31/47
[52] U.S. Cl. ...................................... 424/258; 546/90
[58] Field of Search .......................... 546/90; 424/258

[56] References Cited

U.S. PATENT DOCUMENTS

| 3,287,458 | 11/1966 | Kaminsky et al. | 546/90 |
| 3,849,421 | 11/1974 | Nakagome et al. | 546/90 |
| 4,284,629 | 8/1981 | Grohe et al. | 424/246 |

*Primary Examiner*—Alan L. Rotman
*Attorney, Agent, or Firm*—Thomas L. Johnson; B. Woodrow Wyatt; Paul E. Dupont

[57] ABSTRACT

Novel 5,8-dihydro-8-oxo-1,3-dioxolo[4,5-g]quinoline-7-carboxylic acids substituted in the 5-position by lower-alkylamino or di-lower-alkylamino, useful as antibacterial agents, are prepared from 8-hydroxy-1,3-dioxolo[4,5-g]quinoline-7-carboxylic acid or a lower-alkyl ester thereof via a series of novel intermediates.

21 Claims, No Drawings

1,3-DIOXOLO(4,5-G)QUINOLINE COMPOUNDS

BACKGROUND OF THE INVENTION (1) Field of the Invention

The present invention relates to compounds having the 1,3-dioxolo[4,5-g]quinoline ring system:

[Structure: 1,3-dioxolo[4,5-g]quinoline ring system with numbered positions O(1), (2), (3), (4), (9), (8), (7), (6), (5), N]

It also relates to the use of the compounds as intermediates and antibacterial agents, and to methods for the preparation thereof.

(2) Description of the Prior Art

Certain substituted 1,3-dioxolo[4,5-g]quinolines are known to possess antibacterial activity. Illustrative of these compounds are those of the formula

[Structure with COOH group and N-R substituent]

wherein R is lower-alkyl or other substituents attached through carbon to the nitrogen atom (Kaminsky et al. U.S. Pat. No. 3,287,458, Nov. 22, 1966).

Bayer AG U.S. Pat. No. 4,284,629 (Aug. 18, 1981) discloses certain 4-quinolone-3-carboxylic acids having a tertiary-amino substituent in the 1-position, stated to possess antibacterial activity. Exemplary of the compounds disclosed are 1-dimethylamino-6-nitro-2-methyl-4-quinolone-3-carboxylic acid, methyl ester (Example 4); 1-dimethylamino-7-chloro-6-nitro-2-methyl-4-quinolone-3-carboxylic acid, methyl ester (Example 5); and 1-dimethylamino-7-(n-butylmercapto)-6-nitro-2-methyl-4-quinolone-3-carboxylic acid, methyl ester (Example 17). There is no disclosure of compounds having a methylenedioxy group attached to the phenyl ring.

SUMMARY OF THE INVENTION

In a product aspect the invention relates to compounds of the formula

[Structure I: with COOR" group and R—N—R' substituent]

I where R is hydrogen or alkyl of 1–3 carbon atoms; R' is hydrogen, formyl, alkyl of 1–3 carbon atoms, or alkoxycarbonyl where the alkyl moiety of the latter group is identical with R; and R" is hydrogen or lower-alkyl; and alkali metal or amine salts of compounds where R" is hydrogen.

In a further product aspect, the invention relates to compositions for treatment of bacterial infections in animals, including humans, which comprises an antibacterially effective amount of a compound of Formula I where R is methyl or ethyl, and R' and R" are hydrogen, together with one or more pharmaceutically acceptable excipients.

In a process aspect, the invention relates to a process for preparing compounds of the formula

[Structure with COOR" group and R—N—H substituent]

wherein R is alkyl of 1–3 carbon atoms, and R" is hydrogen or lower-alkyl; or an alkali metal salt thereof where R" is hydrogen, which comprises:

(a) alkylating a compound of the formula

[Structure with COOR" group and H—N—R' substituent]

where R' is formyl or hydrogen, with an alkyl halide of 1–3 carbon atoms in the presence of a base when R' is formyl or an alkali metal carbonate when R' is hydrogen to give, respectively, a compound of the formula

[Structure with COOR" group and R—N—R' substituent] or

[Structure with COOR" group and R—N—COOR substituent]

wherein R is alkyl of 1–3 carbon atoms and R' is formyl; and (b) subjecting the resulting compound to alkaline hydrolysis, and, if desired, converting the resulting alkali metal salt of the product to the free acid (R" is hydrogen).

In a further process aspect, the invention relates to a method for treatment of bacterial infections in animals, including humans, which comprises administering to an animal or human so infected a composition comprising an anti-bacterially effective amount of a compound of Formula I where R is methyl or ethyl, and R and R" are hydrogen.

DETAILED DESCRIPTION INCLUSIVE OF PREFERRED EMBODIMENTS

In the definition of the variables in Formula I above the term "lower-alkyl" in defining R" stands for alkyl preferably having from one to four carbon atoms.

The amino function is introduced into the 5-position of the 1,3-dioxolo[4,5-g]quinoline ring by treatment of the known (U.S. Pat. No. 3,287,458) starting material of the formula

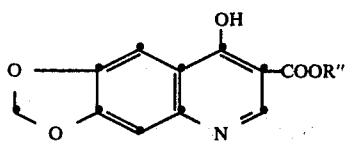

wherein R' is hydrogen or lower-alkyl, with an aminating agent, e.g. an O-arylhydroxylamine such as O-(2,4-dinitrophenyl)-hydroxylamine [2,4-$(O_2N)_2C_6$-$H_3ONH_2$]; cf. Tamura et al., J. Org. Chem. 38, 1239 (1973). The reaction takes place at ambient temperature in an inert organic solvent in the presence of a base such as potassium carbonate, resulting in the formation of the N-amino compound of Formula II below.

The synthesis of the compounds of the invention proceeds in accordance with the following flow-sheet:

The alkylation procedure is carried out either on the primary amino compound (II) or the N-formyl derivative (III). In the case of the former, the alkylation is carried out with an alkyl halide, preferably bromide or iodide, where alkyl has from 1 to 3 carbon atoms, in the presence of an alkali metal carbonate, preferably potassium carbonate, to yield as the product an N-alkyl-N-(alkoxycarbonyl) compound (IV). In the case of the N-formyl derivative, the alkylation is carried out with an alkyl halide in the presence of any strong base, e.g. alkali metal hydroxide, carbonate or alkoxide, the product being an N-alkyl-N-formyl compound (V), where alkyl is methyl, ethyl, propyl or isopropyl. The alkylation reactions take place at a temperature between about 25° C. and 100° C. in an inert organic solvent.

The alkaline hydroysis of a compound of Formula IV or V to form an N-alkyl compound of Formula VI is preferably carried out in aqueous alcoholic solution at a temperature between about 50° C. and 100° C. In the case where R" in compounds of Formula IV or V is lower-alkyl, hydrolysis using two or more molar equivalents of base produces a compound of Formula VI where R" is hydrogen. On the other hand, if only one molar equivalent of base is used, selective hydrolysis of the alkoxycarbonyl or formyl group attached to nitrogen is realized, affording a compound of Formula VI where R" is lower-alkyl.

The compounds of Formulas III, IV and V where R"

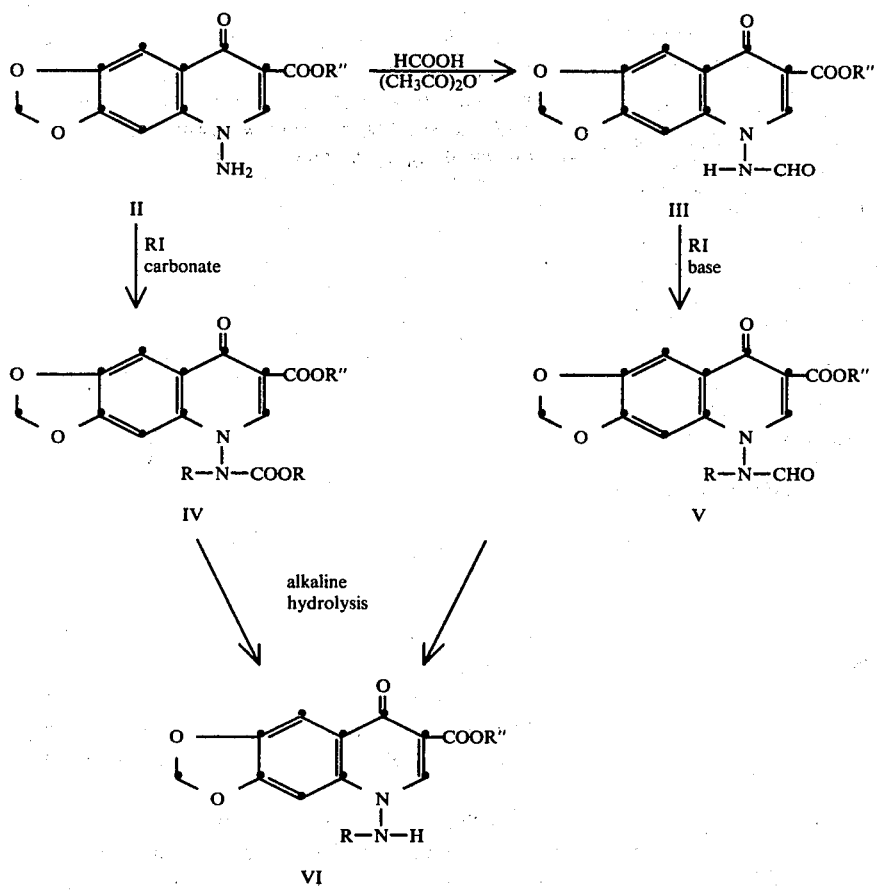

The N-formyl derivative (III) is prepared from the primary amino compound (II) by a conventional formylation procedure using the mixed anhydride derived from formic acid and acetic anhydride.

is lower-alkyl can be readily converted to the respective free acids (R" is hydrogen) by heating with formic acid to effect an ester exchange.

Alkylation of compounds of Formulas II and III where R" is hydrogen will also cause esterification of the carboxyl group to form compounds of Formulas IV and V, respectively, where R" is lower-alkyl.

The compounds of Formula I where both R and R' are alkyl of 1–3 carbon atoms can be prepared by reacting a compound of Formula II with a dialkyl sulfate. The reactants are heated together at a temperature between about 75° C. and 150° C.

The compounds of Formula I where R" is hydrogen can also be prepared and used in the form of their alkali metal or amine salts, preferably the sodium, potassium or N-methylglucamine salts.

The following examples will further illustrate the invention.

EXAMPLE 1

Ethyl 5-amino-5,8-dihydro-8-oxo-1,3-dioxolo[4,5-g]quinoline-7-carboxylate [II; R" is $C_2H_5$]

To a stirred mixture of 12.8 g (0.049 mole) of ethyl 8-hydroxy-1,3-dioxolo[4,5-g]quinoline-7-carboxylate and 13.5 g (0.098 mole) of potassium carbonate in 500 ml of dimethylformamide was added 11.7 g (0.059 mole) of O-(2,4-dinitrophenyl)hydroxylamine. The reaction mixture was stirred overnight at room temperature. An additional 5.0 g of O-(2,4-dinitrophenyl)hydroxylamine and 300 ml of dimethylformamide were then added and stirring was continued again overnight. The solvent was removed in vacuo, the residue stirred in 500 ml of water, and the product was collected by filtration and recrystallized from dimethylformamide to give 7.6 g of ethyl 5-amino-5,8-dihydro-8-oxo-1,3-dioxolo[4,5-g]quinoline-7-carboxylate, pale orange crystals, m.p. 251°–253° C.

EXAMPLE 2

5-Amino-5,8-dihydro-8-oxo-1,3-dioxolo[4,5-g]quinoline-7-carboxylic acid [II; R" is H]

To a solution of 4.4 g (0.11 mole) of sodium hydroxide in 350 ml of water was added 3.0 g (0.047 mole) of ethyl 5-amino-5,8-dihydro-8-oxo-1,3-dioxolo[4,5-g]quinoline-7-carboxylate (Example 1). The resulting slurry was stirred at about 90° C. for three hours, then cooled to room temperature and neutralized with 9.3 ml of acetic acid. The solid product was collected by filtration and recrystallized from dimethylformamide to give 10.3 g of 5-amino-5,8-dihydro-8-oxo-1,3-dioxolo[4,5-g]quinoline-7-carboxylic acid, colorless crystals, m.p. 309°–313° C. (decompn.).

EXAMPLE 3

Ethyl 5-(formylamino)-5,8-dihydro-8-oxo-1,3-dioxolo[4,5-g]quinoline-7-carboxylate [III; R" is $C_2H_5$]

Formic acid (95.7%) (17.35 g, 0.36 mole) was added dropwise to 37.0 g (0.36 mole) of acetic anhydride at 0° C. The mixture was stirred 15 min. at 0° C., 15 min. at 50° C. and again cooled to 0° C. There were then added 10.0 g (0.036 mole) of ethyl 5-amino-5,8-dihydro-8-oxo-1,3-dioxolo[4,5-g]quinoline-7-carboxylate (Example 1) and 10 ml of formic acid. The resulting solution was stirred one hour at 0° C. and at room temperature overnight. The reaction mixture was poured into 400 ml of ice-water, stirred for one hour, and the solid product was collected by filtration and recrystallized from dimethylformamide to give 7 g of product, m.p. 252°–254° C. (decompn.). Further recrystallizations from dimethylformamide and dimethylformamide-ethanol gave a sample of ethyl 5-(formylamino)-5,8-dihydro-8-oxo-1,3-dioxolo[4,5-g]quinoline-7-carboxylate, colorless crystals, m.p. 255°–257° C. (decompn.).

EXAMPLE 4

5-(Formylamino)-5,8-dihydro-8-oxo-1,3-dioxolo[4,5-g]quinoline-7-carboxylic acid [III; R" is H]

A mixture of 5.8 g of ethyl 5-(formylamino)-5,8-dihydro-8-oxo-1,3-dioxolo[4,5-g]-quinoline-7-carboxylate (Example 3) and 100 ml of 97% formic acid was heated at reflux under a Dean-Stark separator for about eight hours. The reaction mixture was then distilled to remove 30 ml of volatiles, cooled and stirred to induce crystallization of product. The latter was collected by filtration and washed with absolute alcohol and ether to give 2.3 g of 5-(formylamino)-5,8-dihydro-8-oxo-1,3-dioxolo[4,5-g]quinoline-7-carboxylic acid, tan crystals, m.p. 302° C. (decompn.).

EXAMPLE 5

Ethyl 5,8-dihydro-5-[(methoxycarbonyl)methylamino]-8-oxo-1,3-dioxolo[4,5-g]quinoline-7-carboxylate [IV; R is $CH_3$, R" is $C_2H_5$]

A mixture of 6.0 g (0.0217 mole) of ethyl 5-amino-5,8-dihydro-8-oxo-1,3-dioxolo[4,5-g]quinoline-7-carboxylate (Example 1), 30.9 g (0.217 mole) of methyl iodide and 30.0 g (0.217 mole) of potassium carbonate in 90 ml of dimethylformamide was stirred at room temperature for 24 hours. The reaction was still incomplete, so an additional 30.9 g of methyl iodide was added and the mixture heated at reflux for 18 hours. The solvent was removed in vacuo and the residue partitioned between chloroform and water. The chloroform layer was dried over anhydrous magnesium sulfate, concentrated and chromatographed on a Waters Prep. 500 HPLC apparatus. There was obtained 6.5 g of product which was recrystallized from ethyl acetate-hexane to give 6 g of ethyl 5,8-dihydro-5-[(methoxycarbonyl)methylamino]-8-oxo-1,3-dioxolo[4,5-g]quinoline-7-carboxylate, colorless crystals, m.p. 142°–145° C.

EXAMPLE 6

Ethyl 5,8-dihydro-5-[(formyl)methylamino]-8-oxo-1,3-dioxolo[4,5-g]quinoline-7-carboxylate [V; R is $CH_3$, R" is $C_2H_5$]

A mixture of 3.0 g (0.01 mole) of ethyl 5-(formylamino)-5,8-dihydro-8-oxo-1,3-dioxolo[4,5-g]quinoline-7-carboxylate (Example 3) and 2.76 g (0.02 mole) of potassium carbonate in 50 ml of dimethylformamide (distilled from calcium hydride) was stirred at room temperature for six hours. Methyl iodide (2.84 g, 0.02 mole) was then added and the resulting slurry was stirred overnight. The solvent was removed in vacuo and the residue partitioned between chloroform and water. The chloroform layer was dried over anhydrous magnesium sulfate, decolorized with charcoal and concentrated to give 3.1 g of solid residue. The latter was recrystallized from acetonitrile to give 2.5 g of ethyl 5,8-dihydro-5-[(formyl)methylamino]-8-oxo-1,3-dioxolo[4,5-g]quinoline-7-carboxylate, colorless crystals, m.p. 242°–244° C.

EXAMPLE 7

5-[(Formyl)methylamino]5,8-dihydro-8-oxo-1,3-dioxolo[4,5-g]-quinoline-7-carboxylic acid [V; R is CH$_3$, R" is H] was prepared by heating ethyl 5,8-dihydro-5-[(formyl)methylamino]-8-oxo-1,3-dioxolo[4,5-g]quinoline-7-carboxylate (Example 6) with formic acid according to the procedure of Example 4, and was obtained in the form of colorless plates, m.p. above 330° C. when precipitated from a solution of its potassium salt by addition of acetic acid.

EXAMPLE 8

Ethyl 5-[ethyl(formyl)amino]-5,8-dihydro-8-oxo-1,3-dioxolo-[4,5-g]quinoline-7-carboxylate [V; R and R" are C$_2$H$_5$] was prepared from 5 g of ethyl 5-(formylamino)-5,8-dihydro-8-oxo-1,3-dioxolo[4,5-g]quinoline-7-carboxylate (Example 3), 4.5 g of potassium carbonate and 3.7 ml of ethyl iodide according to the procedure of Example 6. There was obtained 3.2 g of ethyl 5-[ethyl(formyl)amino]-5,8-dihydro-8-oxo-1,3-dioxolo[4,5-g]-quinoline-7-carboxylate, colorless granules, m.p. 218°-221° C. when recrystallized from ethanol.

EXAMPLE 9

5,8-Dihydro-5-(methylamino)-8-oxo-1,3-dioxolo[4,5-g]quinoline-7-carboxylic acid [VI; R is CH$_3$, R" is H]

A mixture of 4.6 g (0.0132 mole) of ethyl 5,8-dihydro-5-[(methoxycarbonyl)methylamino]-8-oxo-1,3-dioxolo[4,5-g]-quinoline-7-carboxylate (Example 5), 1.6 g (0.0396 mole) of sodium hydroxide and about 100 ml of water was stirred at 95° C. for 4.5 hours. The reaction mixture was cooled, acidified with 5 ml of acetic acid with stirring, and kept in a refrigerator overnight. The solid product was collected by filtration, washed with water and recrystallized from 70 ml of boiling dimethylformamide. There was obtained 3 g of 5,8-dihydro-5-(methylamino)-8-oxo-1,3-dioxolo[4,5-g]quinoline-7-carboxylic acid, colorless crystals, m.p. above 300° C.

EXAMPLE 10

A mixture of 0.6 g (0.0019 mole) of ethyl 5,8-dihydro-5-[(formyl)methylamino]-8-oxo-1,3-dioxolo[4,5-g]quinoline-7-carboxylate (Example 6), 0.30 g (0.0075 mole) of sodium hydroxide and 20 ml of water was heated on a steam bath for two hours. The reaction mixture was cooled to room temperature and 0.6 g of acetic acid was added. The resulting precipitated product was collected by filtration, washed with 100 ml of water and dried in vacuo at 60° C. for one day to give 0.45 g of colorless solid, determined by thin layer chromatography to be identical with compound obtained in Example 9, namely, 5,8-dihydro-5-(methylamino)-8-oxo-1,3-dioxolo[4,5-g]quinoline-7-carboxylic acid.

EXAMPLE 11

Ethyl 5,8-dihydro-5-(methylamino)-8-oxo-1,3-dioxolo[4,5-g]-quinoline-7-carboxylate [VI; R is CH$_3$, R" is C$_2$H$_5$]

To a suspension of 4.1 g (0.013 mole) of ethyl 5,8-dihydro-5-[(formyl)methylamino]-8-oxo-1,3-dioxolo[4,5-g]-quinoline-7-carboxylate (Example 6) in 40 ml of hot absolute ethanol was added a solution of 0.8 g (0.013 mole) of potassium hydroxide (85%) in 2.6 ml of water. The mixture was heated at near the boiling point of the ethanol for about 10 minutes and then chilled in an ice bath. The solid product was collected by filtration and washed with absolute ethanol and ether. After a further washing with water, tetrahydrofuran and ether and drying at 0.1 mm overnight there was obtained 3.1 g of ethyl 5,8-dihydro-5-(methylamino)-8-oxo-1,3-dioxolo[4,5-g]-quinoline-7-carboxylate, colorless crystals, m.p. 211°-218° C.

EXAMPLE 12

5-(Ethylamino)-5,8-dihydro-8-oxo-1,3-dioxolo[4,5-g]quinoline-7-carboxylic acid [VI; R is C$_2$H$_5$, R" is H]

To a stirred suspension of 2 g (0.006 mole) of ethyl 5-[ethyl(formyl)amino]-5,8-dihydro-8-oxo-1,3-dioxolo[4,5-g]-quinoline-7-carboxylate (Example 8) in 53.8 ml of refluxing ethanol was added a solution of 0.9 g (0.014 mole) of potassium hydroxide in 3 ml of water over a period of about two minutes. After a few more minutes of reflux, 30 ml of additional ethanol was added and reflux continued for one hour. The reaction mixture was allowed to stand overnight, then chilled in an ice-bath, and the solid product was collected by filtration and washed with absolute alcohol and ether to give 2 g of 5-(ethylamino)-5,8-dihydro-8-oxo-1,3-dioxolo[4,5-g]-quinoline-7-carboxylic acid in the form of its potassium salt hemihydrate, m.p. 242° C. (decompn.) after being dried for several days at 75° C. (0.1 mm).

EXAMPLE 13

Ethyl 5-[formyl(propyl)amino]-5,8-dihydro-8-oxo-1,3-dioxolo[4,5-g]quinoline-7-carboxylate [V; R is CH$_3$CH$_2$CH$_2$, R' is CH$_2$CH$_3$]

To a stirred mixture of 22.7 g (0.151 mole) of potassium carbonate in 113 ml of dimethylformamide was added 14.7 g (0.048 mole) of ethyl 5-(formylamino)-5,8-dihydro-8-oxo-1,3-dioxolo[4,5-g]quinoline-7-carboxylate (Example 3).

The mixture was stirred for 30 minutes, then a few crystals of potassium iodide were added followed by 33.2 ml (0.36 mole) of propyl bromide. The reaction mixture was stirred in a hot water bath for five hours, then at room temperature overnight, and poured into ice-water. The mixture was extracted three times with chloroform, and the chloroform extracts were washed with water and sodium chloride solution and dried over anhydrous magnesium sulfate. The solution was concentrated *in vacuo* and the solid residue (16.4 g) was slurried in tetrahydrofuran, filtered and washed with tetrahydrofuran and ether. The product was recrystallized from absolute ethanol to give 7.8 g of ethyl 5-[formyl(propyl)amino]-5,8-dihydro-8-oxo-1,3-dioxolo[4,5-g]quinoline-7-carboxylate, colorless crystals, m.p. 188°-192° C.

EXAMPLE 14

5,8-Dihydro-8-oxo-5-(propylamino)-1,3-dioxolo[4,5-g]quinoline-7-carboxylic acid [VI; R is $CH_3CH_2CH_2$, R' is H], was prepared from 4 g (0.012 mole) of ethyl 5-[formyl(propyl)amino]-5,8-dihydro-8-oxo-1,3-dioxolo[4,5-g]quinoline-7-carboxylate (Example 13) and 1.8 g (0.027 mole) of potassium hydroxide in aqueous ethanol, heated at reflux for one hour. The crude product was acidified with acetic acid and the solid product collected and dried to give 3.2 g of 5,8-dihydro-8-oxo-5-(propylamino)-1,3-dioxolo[4,5-g]quinoline-7-carboxylic acid, colorless crystals, m.p. 258°–262° C.

EXAMPLE 15

Ethyl 5,8-dihydro-5-(dimethylamino)-8-oxo-1,3-dioxolo[4,5-g]-quinoline-7-carboxylate [I; R and R' are $CH_3$, R" is $C_2H_5$]

A mixture of 0.5 g of ethyl 5-amino-5,8-dihydro-8-oxo-1,3-dioxolo[4,5-g]quinoline-7-carboxylate (Example 1) and 10 ml of dimethyl sulfate was heated with stirring at 100° C. for 18 hours. The reaction mixture was poured into ice-water and stirred while solid potassium carbonate was added until the mixture was basic. The organic product was extracted with chloroform, and the extracts were dried over anhydrous magnesium sulfate and concentrated. The residue was separated by thin layer chromatography into two fractions which were identified by mass spectroscopy. One fraction was determined to be the mono-methyl compound of Example 11 and the other fraction was identified as the above-entitled dimethyl compound.

The final products of the invention have been found to possess antibacterial activity. The *in vitro* antibacterial activity was determined by conventional serial dilution procedures. Bacterial cultures were grown in tryptose phosphate broth or brain heart infusion broth (containing heat-inactivated normal horse serum for tests with *S. pyogenes*) overnight at 37° C. and subsequently diluted in double strength broth to provide bacterial inocula of about $2 \times 10^5$ cells/ml. Aqueous solutions of the compounds of the invention were prepared by dissolving the free acid form in 0.5 N sodium hydroxide. The solutions were diluted with sterile distilled water to 100 mcg/ml of compound in terms of the free acid. Serial two-fold dilutions of the compound stock solutions were prepared in water and 0.5 ml of each dilution was transferred to sets of tubes, one set for each bacterial inoculum. Each tube was then inoculated with 0.5 ml of the appropriate culture, resulting in a final bacterial concentration of about $1 \times 10^5$ cells/ml. The minimal inhibitory concentration (MIC), defined as the lowest concentration of the test compound to inhibit visible bacterial growth, was recorded after 18–20 hours of static incubation at 37° C. The results are recorded in Table I:

TABLE I

| Bacteria | Minimal Inhibitory Concentration (mcg/ml) Compound Example No. | | |
|---|---|---|---|
| | 9 | 12 | 14 |
| Staphylococcus aureus Smith | 3.9 | >15.6 | >62.5 |
| Streptococcus pyogenes C203 | >500 | >62.5 | >62.5 |
| Escherichia coli Vogel | 0.25 | 1.0 | >7.8 |

TABLE I-continued

| Bacteria | Minimal Inhibitory Concentration (mcg/ml) Compound Example No. | | |
|---|---|---|---|
| | 9 | 12 | 14 |
| Klebsiella pneumoniae 39645 | 1.0 | 1.95 | >7.8 |
| Proteus mirabilis MGH-1 | 0.25 | 1.95 | >7.8 |
| Proteus vulgaris 9920 | 0.125 | 0.25 | 3.9 |
| Pseudomonas aeruginosa MGH-2 | 15.6 | >62.5 | >62.5 |

The *in vivo* antibacterial activity of the compounds of the invention was determined in female mice, 18–20 grams each, by the following procedure:

Aqueous solutions of the compounds to be tested were prepared by dissolving the free acid form in dilute sodium hydroxide and diluting the solution with distilled water to the desired volume.

Cultures of *Escherichia coli* Vogel prepared in brain heart infusion broth, cultures of *Klebsiella pneumoniae* 39645 grown in tryptose phosphate broth with 5% rabbit serum diluted in the same broth were used to infect the mice as follows:

*E. coli*: mice were inoculated intraperitoneally with 0.5 ml of the bacterial test inoculum ($1.87 \times 10^7$ and $5 \times 10^6$ cells/ml respectively).

*K. pneumoniae*: mice were inoculated intramuscularly in the right hind leg with 0.2 ml of the bacterial test inoculum ($2.05 \times 10^4$ cells/ml).

Mice infected with *E. coli* were medicated once (0.5 ml) one-half hour post infection, the test compound being administered by the subcutaneous (s.c.) route. Deaths were recorded daily for seven days.

Mice infected with *K. pneumoniae* were medicated at the following times: seventeen hours and one hour preinfection, six hours postinfection and twice a day for the next three days. The test compound was administered by the subcutaneous (0.2 ml) route. Deaths were recorded daily for fourteen days.

Groups of ten animals each for four or five dose levels were thus treated and the number of survivors in each group recorded. The fifty percent protective dose values ($PD_{50}$) were then calculated. The results obtained are given in Table II:

TABLE II

| Compound Example No. | Protective Dose ($PD_{50}$, mg/kg) | |
|---|---|---|
| | E. coli | K. pneumoniae |
| 9 | 3.3 | 28 |
| 12 | 7.0 | 50 |
| 14 | 141 | >200 |

The antibacterial activity of the compounds of Formula VI (R" is H) decreases as the carbon content of the group R increases. Thus the preferred compound is that of Example 9, namely, 5,8-dihydro-5-(methylamino)-8-oxo-1,3-dioxolo[4,5-g]quinoline-7-carboxylic acid.

The intermediates for the compounds of Formula VI are mostly inactive as antibacterial agents. The compound of Example 2 had some *in vitro* activity (MIC 7.8, 3.9 and 3.9 against *E. coli, P. mirab.* and *P. vulg.*, respectively); and the compound of Example 7 was active *in vitro* against *E. coli, K. pneum., P. mirab.* and *P. vulg.* (MIC 31.3, 15.6, 7.8 and 15.6, respectively) and had a $PD_{50}$ value of 40 *in vivo* against *E. coli*.

The antibacterially active compounds of the invention can be prepared for use by conventional pharmaceutical procedures: that is, by dissolving or suspending them in a pharmaceutically acceptable vehilce, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

We claim:

1. A compound of the formula

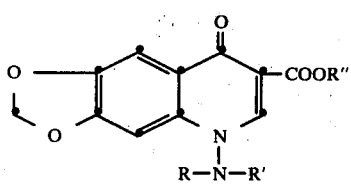

where R is hydrogen or alkyl of 1-3 carbon atoms; R' is hydrogen, formyl, alkyl of 1-3 carbon atoms, or alkoxycarbonyl where the alkyl moiety of the latter group is identical with R; and R" is hydrogen or lower-alkyl; or an alkali metal salt or N-methylglucamine salt of a compound where R" is hydrogen.

2. A compound according to claim 1 where R' and R" are hydrogen, and R is alkyl of 1-3 carbon atoms.

3. 5,8-Dihydro-5-(methylamino)-8-oxo-1,3-dioxolo[4,5-g]quinoline-7-carboxylic acid, according to claim 2.

4. 5-(Ethylamino)-5,8-dihydro-8-oxo-1,3-dioxolo[4,5-g]quinoline-7-carboxylic acid, according to claim 2.

5. 5-Amino-5,8-dihydro-8-oxo-1,3-dioxolo[4,5-g]-quinoline-7-carboxylic acid, according to claim 1.

6. 5,8-Dihydro-8-oxo-5-(propylamino)-1,3-dioxolo[4,5-g]quinoline-7-carboxylic acid, according to claim 2.

7. A compound according to claim 1 where R' is formyl.

8. Ethyl 5,8-dihydro-5-[(formyl)methylamino]-8-oxo-1,3-dioxolo[4,5-g]quinoline-7-carboxylate, according to claim 7.

9. Ethyl 5-(formylamino)-5,8-dihydro-8-oxo-1,3-dioxolo[4,5-g]quinoline-7-carboxylate, according to claim 7.

10. Ethyl 5-[ethyl(formyl)amino]-5,8-dihydro-8-oxo-1,3-dioxolo[4,5-g]quinoline-7-carboxylate, according to claim 7.

11. 5-[(Formyl)methylamino]-5,8-dihydro-8-oxo-1,3-dioxolo[4,5-g]quinoline-7-carboxylic acid, according to claim 7.

12. 5-(Formylamino)-5,8-dihydro-8-oxo-1,3-dioxolo[4,5-g]quinoline-7-carboxylic acid, according to claim 7.

13. Ethyl 5-[formyl(propyl)amino]-5,8-dihydro-8-oxo-1,3-dioxolo[4,5-g]quinoline-7-carboxylate, according to claim 7.

14. Ethyl 5-amino-5,8-dihydro-8-oxo-1,3-dioxolo[4,5-g]quinoline-7-carboxylate, according to claim 1.

15. Ethyl 5,8-dihydro-5-[(methoxycarbonyl)methylamino]-8-oxo-1,3-dioxolo[4,5-g]quinoline-7-carboxylate, according to claim 1.

16. Ethyl 5,8-dihydro-5-(methylamino)-8-oxo-1,3-dioxolo[4,5-g]quinoline-7-carboxylate, according to claim 1.

17. The process for preparing a compound of the formula

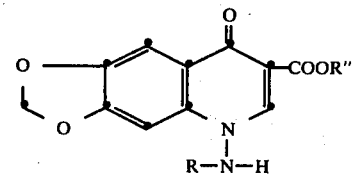

wherein R is alkyl of 1-3 carbon atoms, and R" is hydrogen or lower-alkyl; or an alkali metal salt thereof where R" is hydrogen, which comprises:

(a) alkylating a compound of the formula

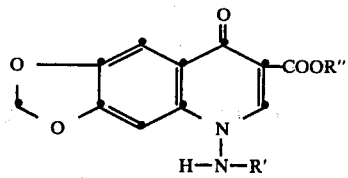

where R' is formyl or hydrogen, with an alkyl halide of 1-3 carbon atoms in the presence of a base when R' is formyl or an alkali metal carbonate when R' is hydrogen to give, respectively, a compound of the formula

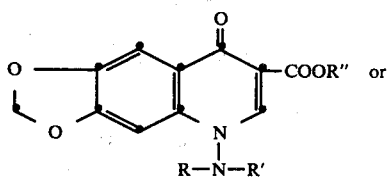

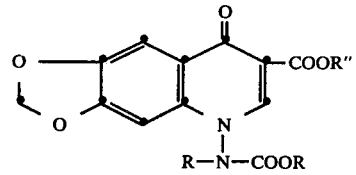

wherein
R is alkyl of 1-3 carbon atoms, R' is formyl and R" is lower-alkyl; and (b) subjecting the resulting compound to alkaline hydrolysis; and, if desired, converting the resulting alkali metal salt of the product to the free acid (R" is hydrogen).

18. A composition for treatment of bacterial infections in animals, including humans, which comprises an antibacterially effective amount of a compound according to claim 2, together with one or more pharmaceutically acceptable excipients.

19. A composition according to claim 18 wherein the antibacterially effective compound is 5,8-dihydro-5-methylamino-8-oxo-1,3-dioxolo[4,5-g]quinoline-7-carboxylic acid.

20. A method for treatment of bacterial infections in animals, including humans, which comprises administering parenterally or orally to an animal or human so infected an antibacterially effective amount of a composition according to claim 18.

21. A method according to claim 20 wherein the antibacterially active compound is 5,8-dihydro-5-methylamino-8-oxo-1,3-dioxolo[4,5-g]quinoline-7-carboxylic acid.

* * * * *

UNITED STATES PATENT AND TRADEMARK OFFICE
CERTIFICATE OF CORRECTION

PATENT NO. : 4,439,436
DATED : March 27, 1984
INVENTOR(S) : Mark P. Wentland & Denis M. Bailey It is certified that error appears in the above-identified patent and that said Letters Patent is hereby corrected as shown below:

Column 3, line 18, " R' " should read --R"--.

Column 9, line 47, "100 mcg/ml" should read --1000 mcg/ml--.

Column 11, line 4, "vehilce" should read --vehicle--.

Signed and Sealed this

Fourth Day of September 1984

[SEAL]

Attest:

GERALD J. MOSSINGHOFF

Attesting Officer — Commissioner of Patents and Trademarks